(12) United States Patent
Löfgren et al.

(10) Patent No.: US 12,420,039 B2
(45) Date of Patent: Sep. 23, 2025

(54) DEVICE FOR A RESPIRATION ARRANGEMENT

(71) Applicant: Monivent AB, Gothenburg (SE)

(72) Inventors: Mikael Löfgren, Mölndal (SE); Antti Stålnacke, Surte (SE)

(73) Assignee: Monivent AB, Gothenburg (SE)

( * ) Notice: Subject to any disclaimer, the term of this patent is extended or adjusted under 35 U.S.C. 154(b) by 663 days.

(21) Appl. No.: 17/792,959

(22) PCT Filed: Jan. 20, 2021

(86) PCT No.: PCT/EP2021/051179
§ 371 (c)(1),
(2) Date: Jul. 14, 2022

(87) PCT Pub. No.: WO2021/148457
PCT Pub. Date: Jul. 29, 2021

(65) Prior Publication Data
US 2023/0033221 A1 Feb. 2, 2023

(30) Foreign Application Priority Data
Jan. 23, 2020 (SE) .................................... 2050064-1

(51) Int. Cl.
*A61M 16/00* (2006.01)
*A61M 16/06* (2006.01)
*A61M 16/08* (2006.01)

(52) U.S. Cl.
CPC .... *A61M 16/0084* (2014.02); *A61M 16/0605* (2014.02); *A61M 16/0875* (2013.01); *A61M 2016/0027* (2013.01); *A61M 2240/00* (2013.01)

(58) Field of Classification Search
CPC .......... A61M 16/0084; A61M 16/0605; A61M 16/0875; A61M 16/0858; A61M 16/0816;
(Continued)

(56) References Cited

U.S. PATENT DOCUMENTS 4,037,595 A * 7/1977 Elam ........................ A62B 9/02
128/205.24
4,360,017 A 11/1982 Barlett
(Continued)

FOREIGN PATENT DOCUMENTS

CA 2863047 A1 * 7/2013 ........... A61B 5/0803
CN 2665674 Y 12/2004
(Continued)

OTHER PUBLICATIONS

English language translation of Chinese Search Report dated Sep. 18, 2024 for Chinese Application No. 202180009148.X, 3 pages.
(Continued)

*Primary Examiner* — Brandy S Lee
*Assistant Examiner* — Sydney Reyes Russell
(74) *Attorney, Agent, or Firm* — RMCK Law Group, PLC

(57) ABSTRACT

The present invention relates to a device for a respiration arrangement. The device comprises a conduit having a first opening connectable to an air/gas source such as a resuscitation bag, and a second opening connectable to a face mask, such that a fluid pathway along a longitudinal direction of the conduit is established from the first opening to the second opening. The device further comprises a flow constriction, arranged in the conduit which upon fluid flow through the conduit results in a pressure difference over the flow constriction, the flow constriction at least partly comprising a laminar flow section, wherein the device further comprises at least one pressure connecting port arranged in pressurized communication with fluid between the flow constriction and the first opening, and wherein the pressure connecting port is arranged in the longitudinal direction of the conduit.

16 Claims, 5 Drawing Sheets

(58) Field of Classification Search
CPC ... A61M 2016/0033; A61M 2016/0039; G01F 1/36; A61B 5/087
See application file for complete search history.

(56) References Cited

U.S. PATENT DOCUMENTS

| | | | |
|---|---|---|---|
| 4,966,141 | A | 10/1990 | Bacaner et al. |
| 5,546,935 | A | 8/1996 | Champeau |
| 6,152,132 | A | 11/2000 | Psaros |
| 6,224,560 | B1* | 5/2001 | Gazula .................. A61B 5/087 |
| | | | 128/204.23 |
| 8,192,367 | B2 | 6/2012 | Myklebust et al. |
| 2004/0254491 | A1 | 12/2004 | Ricciardelli |
| 2006/0032808 | A1 | 2/2006 | Hauge |
| 2008/0245368 | A1 | 10/2008 | Dunsmore et al. |
| 2009/0139530 | A1* | 6/2009 | Landis .............. A61M 16/0858 |
| | | | 128/207.15 |
| 2010/0168599 | A1* | 7/2010 | Esposito ........... A61M 16/0858 |
| | | | 600/532 |
| 2010/0218769 | A1 | 9/2010 | Boussignac |
| 2010/0229865 | A1 | 9/2010 | Boussignac |
| 2010/0282262 | A1 | 11/2010 | Boussignac |
| 2012/0255551 | A1 | 10/2012 | Boussignac |
| 2012/0304985 | A1* | 12/2012 | Lalonde ............ A61M 16/0069 |
| | | | 128/205.24 |
| 2013/0146053 | A1* | 6/2013 | Mazela ............. A61M 16/0858 |
| | | | 137/15.01 |
| 2013/0291868 | A1 | 11/2013 | Boussignac |
| 2015/0068519 | A1 | 3/2015 | Bambrilla et al. |
| 2016/0058969 | A1 | 3/2016 | Winter et al. |
| 2016/0175548 | A1 | 6/2016 | Spence et al. |
| 2017/0266399 | A1 | 9/2017 | Campana et al. |
| 2018/0369459 | A1 | 12/2018 | Abate et al. |

FOREIGN PATENT DOCUMENTS

| | | |
|---|---|---|
| DE | 102008028662 A1 | 12/2008 |
| EP | 1674123 A1 | 6/2006 |
| WO | 2015167388 A1 | 11/2015 |
| WO | 2018236228 A1 | 12/2018 |

OTHER PUBLICATIONS

English language translation of First Chinese Office Action dated Sep. 20, 2024 for Chinese Application No. 202180009148.X, 10 pages.
PCT International Search Report and Written Opinion for International Application No. PCT/EP2021/051179 mailed May 3, 2021, 11 pages.
Swedish Office Action for SE Application No. 2050064-1 mailed Dec. 14, 2021, 6 pages.
Swedish Office Action for SE Application No. 2050064-1 mailed Sep. 15, 2020, 7 pages.
Swedish Office Action and Search Report for SE Application No. 2150055-8 mailed Mar. 4, 2021, 9 pages.
Swedish Office Action for SE Application No. 2150055-8 mailed May 19, 2022, 5 pages.
Swedish Search Report for SE Application No. 2050064-1 mailed Sep. 15, 2020, 3 pages.
Extended European Search Report dated Mar. 27, 2024 for EP Application No. 23215448.4, 7 pages.

* cited by examiner

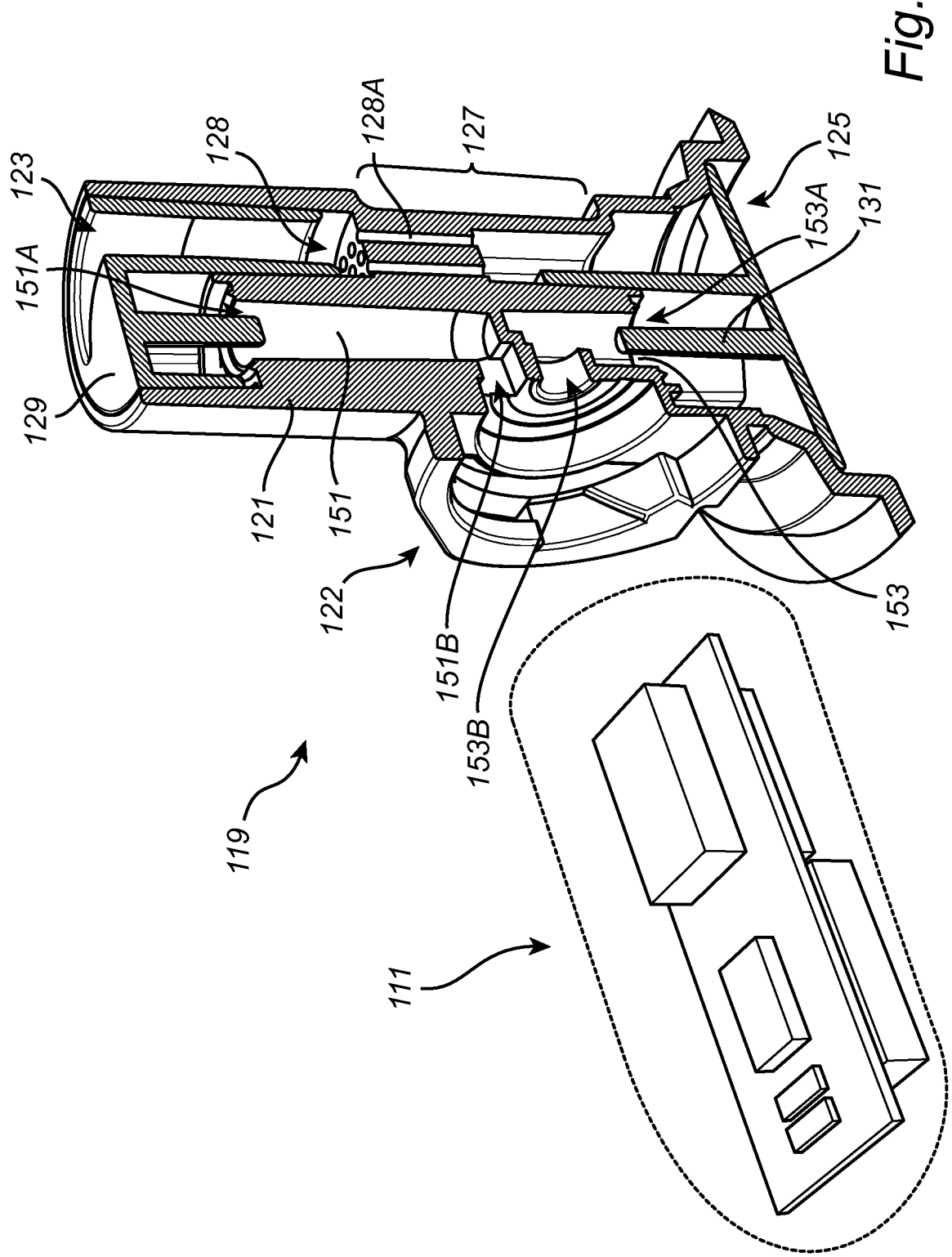

DEVICE FOR A RESPIRATION ARRANGEMENT

CROSS-REFERENCE TO RELATED APPLICATIONS

This application is a 371 U.S. National Stage of International Application No. PCT/EP2021/051179, filed Jan. 20, 2021, which claims priority to Swedish Patent Application No. 2050064-1, filed Jan. 23, 2020. The disclosures of each of the above applications are incorporated herein by reference in their entirety.

FIELD OF THE INVENTION

The present inventive concept relates to a device for a respiration arrangement, typically for breathing support to patients, preferably infants. The present inventive concept also relates to a respiration arrangement comprising a patient interface such as e.g. a face mask, an air/gas source, and the device.

BACKGROUND OF THE INVENTION

At birth, an infant may require immediate support in order to initiate breathing or support to sustain breathing. This may be the case due to apnea, airway obstruction, respiratory distress syndrome or when the infant is prematurely born due to their immature respiratory system. Sometimes the infant is in need of immediate breathing support directly after birth, which is normally carried out by manually pumping air into the lungs of the infant. Breathing support, or manual ventilation, may also be performed in other situations, and can be conducted on any patient regardless of his or her age.

A respiration device, or respiration arrangement, typically includes a patient interface such as e.g. a face mask to fit over the nose and mouth of the patient, an endotracheal tube, a laryngeal mask or nasal prongs, an air source (or another gas source, e.g. oxygen), and an air pathway providing the air from the air source to the face mask. The air source may e.g. be a resuscitation bag/bellow. In many situations, there is a need for monitoring the patient's respiration, or measuring the ventilation of a patient not breathing. Thus, there is a need to know the amount of air fed to the patient. The monitoring is typically performed by a monitoring arrangement arranged along the air pathway, including a flow sensor using e.g. a pressure sensor, such as a differential pressure sensor, for determining the flow of air, and a display disclosing information of the respiration. An example of such resuscitation arrangement is disclosed in WO 2015/167388 A1.

Flow sensors are typically based on the Venturi principle, which means that the pressure drop associated with a flow constriction in the air pathway is measured. An algorithm transforming the differential pressure to a flow is typically carried out by the means of a processor or CPU and a memory. In order to achieve a high level of accuracy of the flow measurement, the flow sensor needs to be carefully designed with regards to e.g. the geometry of the flow constriction.

Due to the risk of cross-contamination between patients, single-use units are preferred for those parts being subject to be contaminated by the patient. Thus, there is a drive to keep components costs as low as possible. However, as accuracy of the flow measurement is of high importance, there is often a conflict between costs and accuracy. There is thus a need in the industry for a respiration arrangement, and associated parts, which better balance the cost and measurement accuracy.

SUMMARY

An object of the inventive concept is to overcome the above problems, and to provide a device which, at least to some extent, is less complex than prior art solutions, while still enabling a sufficient measurement accuracy. This, and other objects, which will become apparent in the following, are accomplished by means of a device for a respiration arrangement, and a respiration arrangement comprising such device as defined in the accompanying claims.

The present inventive concept is based on the insight that a more accurate flow measurement can be performed by controlling the fluid flow to, and/or in, the flow constriction in the air pathway when fluid flows from the air/gas source to the patient interface (e.g. a face mask, endotracheal tube, laryngeal mask or nasal prongs) or in the opposite direction, from the patient interface to the air/gas source. For example, the fluid may be controlled by a flow guiding element guiding flow towards the flow constriction and/or by providing the flow constriction with a laminar flow section.

According to at least a first aspect of the present inventive concept, a device for a respiration arrangement is provided. The device comprises:
  a conduit having a first opening connectable to an air/gas source such as a resuscitation bag, and a second opening connectable to a patient interface, such that a fluid pathway along a longitudinal direction of the conduit is established from the first opening to the second opening;
  a flow constriction, arranged in the conduit which upon fluid flow through the conduit results in a pressure difference over the flow constriction, wherein the device further comprises at least one flow guiding element arranged in the conduit between the first opening and the flow constriction, and configured to guide fluid flow to the flow constriction.

Hereby, any accuracy problem originating from the flow measurement with regards to asymmetrical flow constrictions, as e.g. flow constrictions not being centrally arranged in the conduit, or flow constrictions causing an undesired turbulence of the flow, can be avoided or at least reduced. Thus, the flow guiding element enables accurate measurement independently of the orientation of the incoming fluid flow as it guides the fluid flow towards the flow constriction. Furthermore, as the flow guiding element occupies space inside the conduit, it contributes in reducing undesired dead space inside the device, thereby improving the respiration procedure.

It should be noted that the device may e.g. be an adapter, such as an airway adapter, which is detachably arranged to the patient interface (e.g. a face mask) of the respiration arrangement. As an alternative, the device may form a part of, or comprise, an integrated patient interface, e.g. in the form of a face mask, endotracheal tube, laryngeal mask or nasal prongs, attached to the conduit at an end portion comprising the second opening. The device may also be referred to as a respiration device, a conduit arrangement, or an air transportation arrangement. For embodiments in which the patient interface is a face mask, the face mask may e.g. be a soft mask and the device forming part of a hard mask, or an adapter, connectable to the soft mask.

In the following, the patient interface is mainly referred to as a face mask, but it should be understood that it may as well be another patient interface, such as e.g. endotracheal tube, a laryngeal mask or nasal prongs. Thus, when stating that the second opening is connectable to a face mask, it may as well be connectable to another patient interface, such as the endotracheal tube, the laryngeal mask or the nasal prongs. The face mask, the endotracheal tube, the laryngeal mask and the nasal prongs may be referred to as patient interfaces, as they serve as an interface between the second opening of the conduit of the device, and the patient.

It should be understood that the conduit provides an air/gas pathway in both directions, i.e. both from the air/gas source to the face mask via the first opening, the conduit and the second opening in that order, and from the face mask to the air/gas source via the second opening, the conduit and the first opening in that order. In the former case, the first opening acts as a conduit inlet and the second opening acts as a conduit outlet, and the flow constriction is arranged downstream of the inlet. In the other case, when the fluid flows from the face mask to the air/gas source, typically as the patient exhales, the second opening acts as conduit inlet and the first opening acts as conduit outlet. The exhaled air/gas is then typically ventilated out from the respiration arrangement. Hence, the flow guiding element is, upon fluid flow from the first opening to the second opening, arranged and configured to guide fluid flow towards, or to, the flow constriction. When fluid is flowing in the opposite direction, i.e. from the second opening to the first opening, fluid is transported through the flow guiding element in a reverse direction, i.e. from the flow constriction towards the first opening. Thus, the flow guiding element may be arranged and configured to transport the flow through the flow guiding element. In other words, the flow guiding element may comprise a channel or fluid passage enabling fluid flow between the first opening and the flow constriction, and between the flow constriction and the first opening. According to at least one example embodiment, the conduit comprises the conduit walls surrounding the air/gas pathway. That is, the conduit walls are formed of a separate element (or separate part) compared to the flow guiding element, or stated differently, the conduit walls and the flow guiding elements are separate elements (or separate parts). For example, the conduit with its conduit walls may be physically separated from the flow guiding element prior to insertion of the latter into the conduit. Hereby, the conduit and its conduit walls may be manufactured separately to the flow guiding element. After insertion of the flow guiding element into the conduit, the flow guiding element is typically in contact with the conduit walls, e.g. by a press-fit or by some type of welding or other contacting means. As the conduit and its conduit walls form a separate element (or part) compared to the flow guiding element, the flow guiding element may be detachably arranged in the conduit.

Furthermore, the flow constriction which is arranged in the conduit to, upon fluid flow through the conduit, result in a pressure difference over the flow constriction, is designed so that the pressure difference regardless of the direction of the fluid flow (from air/gas source to face mask, or vice versa) can be used for e.g. flow measurement. That is, the flow of air/gas provided to the face mask from the air/gas source can be measured, as well as the flow of air/gas from the face mask, caused by exhalation of the patient, towards the air/gas source. By measuring the flow in both directions, the amount of leakage in the system can be determined.

According to at least one example embodiment, the flow guiding element is detachably arranged to the conduit. Thus, the flow guiding element can be removed upon will from the conduit via the first opening e.g. for maintenance or adaptation reasons, and then subsequently be refitted into the conduit. That the flow guiding element is detachably arranged to the conduit may alternatively, or additionality, imply that the flow guiding element may be removed from the conduit after use and e.g. be recycled or otherwise re-used. Thus, the flow guiding element is typically attached to the conduit, e.g. by being press-fitted into the conduit and/or welded or otherwise connected to the conduit walls, but may be de-attached from the conduit by simply pulling the flow guiding element out of the conduit possibly subsequent to removing any welds or other connector (if present) of the flow guiding element to the conduit walls.

According to at least one example embodiment the air/gas source is a resuscitation bag or a T-piece resuscitator. Alternatively, air/gas source may be an air source or another gas source, such as e.g. an oxygen source. Thus, the conduit of the device is preferably at the end portion comprising the first opening arranged and configured to be connected to the air/gas source, such as a resuscitation bag.

According to at least one example embodiment, the device comprises at least one pressure connecting port arranged in pressurized communication with fluid between the flow constriction and the first opening, the pressure connecting port being connectable to a pressure sensor for measuring fluid pressure.

According to at least one example embodiment, the device comprises at least one pressure connecting port arranged in pressurized communication with fluid between the flow constriction and the first opening, the pressure connecting port being connectable to a pressure sensor for measuring fluid pressure, and wherein the pressure connecting port is arranged in the longitudinal direction of the conduit.

Hereby, the at least one pressure connecting port and the flow constriction have fluid pathways arranged in the same direction (the longitudinal direction of the conduit), which facilitate manufacturing (e.g. by injection molding) of the device. Moreover, by such orientation of the at least one pressure connecting port, a filter, such as a bacterial filter, may easily be inserted into the device, and further into the pressure connecting port, via the first opening.

It should be understood that when stating that the at least one pressure connecting port is arranged in the longitudinal direction of the conduit, the cross section of an inlet of the at least one pressure connecting port is arranged perpendicular to the longitudinal direction. Or stated differently, the at least one pressure connecting port comprises an inlet facing a geometrical plane being perpendicular to the longitudinal direction. However, it should be noted that the inlet of the at least one pressure connecting port is not arranged in the conduit to receive any fluid flow, but rather to act as a port for enabling fluid communication enabling measurement of the pressure of the fluid between the flow constriction and the first opening (i.e. upstream of the flow constriction when fluid flows from the first opening to the second opening). Stated differently, the at least one pressure connecting port comprises an elongated fluid cavity having a longitudinal axis being parallel to the longitudinal direction of the conduit.

According to at least one example embodiment, the flow guiding element is configured to guide fluid flow away from the pressure connecting port. For example, the flow guiding element may comprise a flow passage guiding flow away from the pressure connecting port, towards the flow constriction.

The at least one pressure connecting port may according to at least one example embodiment simply be referred to as a pressure port.

According to at least one example embodiment, the at least one pressure connecting port is at least partly arranged in parallel to the flow constriction. Hereby, the device may be made more compact.

According to at least one example embodiment, the flow constriction at least partly comprises a laminar flow section having a plurality of elongated channels arranged in the longitudinal direction of the conduit such that the at least one pressure connecting port and the plurality of elongated channels are arranged at least partly in parallel.

Thus, manufacturing of the device is facilitated owing to the coherent direction of the fluid channels of the at least one pressure connecting port and the elongated channels. Moreover, by arranging the at least one pressure connecting port and the plurality of elongated channels at least partly in parallel, the device may be made more compact, as a cross section of the conduit perpendicular to the longitudinal direction, at the flow constriction, comprises both the at least one pressure connecting port and the elongated channels. In other words, at least a part of the pressure connecting port is sharing the same conduit space as the flow constriction. By such configuration, the flow constriction is typically asymmetrical arranged in the conduit, and the flow guiding element may serve its purpose by directing the fluid flow towards the flow constriction. Without such flow guiding element, fluid would be able to flow into the pressure connecting port and thereby reduce the measurement accuracy.

It should be understood that each channel in the plurality of elongated channels has a main direction in the longitudinal direction. The elongated channels may be referred to as elongated holes or tubes. The number, and the length of the channels, are typically adapted based on the expected fluid flow through the flow constriction with the purpose to achieve a laminar flow instead of a turbulent flow, as this improves the measurement accuracy. How to design the laminar flow section in order to achieve a laminar flow is known to the skilled person. It should also be noted that as the laminar flow condition is at least partly dependent on the fluid flow, where a high fluid flow increases the risk of turbulence occurrence, fluid flow in at least a part of the elongated channels may still at times be turbulent. According to at least one example embodiment, the laminar flow section may simply be referred to as a flow section.

Typically, the laminar flow section constitutes at least a portion of the flow constriction, and thus fully accommodate the passageway in the flow constriction, in at least a part along the longitudinal direction of the conduit. According to at least one example embodiment, the laminar flow section is the flow constriction of the device.

According to at least one example embodiment, the laminar flow section comprises a net having a plurality of holes, instead of the elongated channels. Thus, such net serves the same purpose as the elongated channels, i.e. to provide a laminar flow.

It should be understood that the purpose of the laminar flow section is to provide a relatively large contact surface between the internal walls of the elongated channels and the fluid, which results in a more linear relation between fluid flow and pressure drop, thereby improving measurement accuracy.

According to at least a second aspect of the present inventive concept, another device for a respiration arrangement is provided. The device comprises:

a conduit having a first opening connectable to an air/gas source such as a resuscitation bag, and a second opening connectable to a patient interface, such that a fluid pathway along a longitudinal direction of the conduit is established from the first opening to the second opening;

a flow constriction arranged in the conduit which upon fluid flow through the conduit results in a pressure difference over the flow constriction, wherein the flow constriction at least partly comprises a laminar flow section, wherein the device further comprises at least one pressure connecting port arranged in pressurized communication with fluid between the flow constriction and the first opening, the pressure connecting port being connectable to a pressure sensor for measuring fluid pressure, and wherein the pressure connecting port is arranged in the longitudinal direction of the conduit.

Thus, the second aspect of the inventive concept is very similar to the first aspect of the inventive concept, but instead of (in its broadest concept) providing a flow guiding element guiding the flow towards the flow constriction, the flow inside the flow constriction is controlled by a laminar flow section, and the pressure connecting port. Thus, effects and features related to the pressure connecting port and laminar flow section of this second aspect of the present inventive concept are largely analogous to those described above in connection with the first aspect of the inventive concept.

According to at least one example embodiment, the device of the second aspect of the inventive concept comprises at least one flow guiding element as previously described.

Hereafter, embodiments related to both the first and second aspects of the inventive concept are described in detail. It should be understood that each embodiment may be related to the first aspect of the inventive concept and the second aspect of the inventive concept, separately.

According to at least one example embodiment, the flow guiding element comprises:

a shielding portion arranged in the conduit to cover an inlet of the pressure connecting port, a fluid passage enabling fluid flow between the first opening and the flow constriction, and at least one pressure conduit arranged to provide a fluid channel between the fluid passage and the pressure connecting port.

Hereby, fluid flow into, or through, the pressure connecting port can be avoided by the shielding portion, while still providing a fluid passage, which is guided towards the flow constriction (typically towards the laminar flow section). Thus, the pressure connecting port can be in fluid communication, without receiving any fluid flow, with fluid present between the first opening and the flow constriction via the at least one pressure conduit (i.e. upstream conditions of the flow constriction when fluid flows through the device from the first opening to the second opening). Thus, the pressure of the fluid can be measured by a pressure sensor connected to the pressure connecting port.

According to at least one example embodiment, the fluid passage is shaped to enable a minimum flow resistance, e.g. by having a crescent shaped cross section perpendicular to the longitudinal direction of the conduit. Hereby, the breathing support to the patient is improved. Thus, a majority of the cross section of the flow guiding element not used as shielding portion, can be used for the fluid passage.

According to at least one example embodiment, the at least one pressure conduit is arranged in proximity to an end portion of the fluid passage in order to minimize influence of potential fluid turbulence. According to at least one example embodiment, the flow guiding element comprises at least two pressure conduits in order to decrease measurement errors.

According to at least one example embodiment, the pressure connecting port is a first pressure connecting port, and the device further comprises a second pressure connecting port arranged in pressurized communication with fluid between the flow constriction and the second opening, such that a differential pressure sensor can be connected to the first and second pressure connecting ports for measuring the differential pressure over the flow constriction.

Hereby, the flow through the flow constriction can be measured by e.g. a flow sensor based on the Venturi principle or Bernoulli equation, which means that the pressure drops associated with a flow constriction in the air pathway is measured. An algorithm transforming the differential pressure to a flow is may be carried out by the means of a processor or CPU and a memory.

According to at least one example embodiment, the second pressure connecting port is arranged in the longitudinal direction of the conduit. Thus, a cross section of an inlet of the second pressure connecting port is arranged perpendicular to the longitudinal direction. Stated differently, the second pressure connecting port comprises an elongated fluid cavity having a longitudinal axis being parallel to the longitudinal direction of the conduit.

According to at least one example embodiment, the device comprises a pressure sensor connecting portion arranged between the first opening and the second opening, typically close to the flow constriction. The pressure sensor connecting portion is connectable to a pressure sensor unit. Typically, the pressure sensor connecting portion comprises a tube-shaped portion extending from the conduit perpendicular to the longitudinal direction. Moreover, according to at least one example embodiment, the first and second pressure connecting ports are arranged in the device to have respective openings (which may be referred to as outlets of the pressure connecting ports) in the pressure sensor connecting portion, each of the openings having a cross section parallel to the longitudinal direction. Such openings are thus arranged in the opposite end to the opening of the respective pressure connecting port which have a cross section perpendicular to the longitudinal direction of the conduit (i.e. the openings which were referred to as inlets of the pressure connecting ports). That is, each one of the first and second pressure connecting ports may have an L-shaped channel.

According to at least one example embodiment, fluid flow in the pressure connecting ports is minimized, at least fluid flow through the respective pressure connecting port. Hereby, any contamination which may enter into the device will not propagate into a connected pressure sensor.

According to at least one example embodiment, the flow guiding element is a first flow guiding element and the device further comprises a second flow guiding element arranged in the conduit between the flow constriction and the second opening, and configured to guide fluid flow away from the second pressure connecting port.

Thus, when fluid flows from the second opening to the first opening of the conduit (i.e. when the patient exhales and fluid flows in a direction from the patient interface towards the air/gas source), the fluid is guided towards the flow constriction in a similar manner as described above in relation to the first flow guiding element. Hence, the second flow guiding element is, upon fluid flow from the second opening to the first opening, arranged and configured to guide fluid flow towards, or to, the flow constriction. When fluid is flowing in the opposite direction, i.e. from the first opening to the second opening, fluid is transported through the second flow guiding element in a reverse direction, i.e. from the flow constriction towards the second opening. Hereby, any accuracy problem originating from the flow measurement with regards to asymmetrical flow constrictions, as e.g. flow constrictions not being centrally arranged in the conduit, or flow constrictions causing an undesired turbulence of the flow, can be avoided or at least reduced. Thus, the second flow guiding element enables accurate measurement independently of the orientation of the incoming fluid flow as it guides the fluid flow towards the flow constriction, and away from the second pressure connecting port. Furthermore, as the second flow guiding element occupies space inside the conduit, it contributes in reducing undesired dead space inside the device, thereby improving the respiration procedure. This is especially important for embodiments having a laminar flow section as the large contact area between inner walls of the laminar flow section and fluid flow typically leads to an increased dead space. Thus, the dead space reduction owing to the flow guiding element(s) counteract the increased dead space resulting from the laminar flow section.

According to at least one example embodiment, the second flow guiding element acts as a protector preventing any liquid (saliva, vomit) expectorated from the patient to reach further into the conduit, thereby preventing contaminations to propagate further into the device. This is especially important for embodiments having a laminar flow section as the narrow passageway(s) otherwise could be clogged. According to at least one example embodiment, the second flow guiding element comprises a shielding portion arranged in the conduit to cover an inlet of the second pressure connecting port, a fluid passage enabling fluid flow between the second opening and the flow constriction, at least one pressure conduit arranged to provide a fluid channel between the fluid passage and the second pressure connecting port, and a protecting portion arranged in the conduit to prevent any liquid expectorated from the patient to reach further into the conduit.

Thus, the second flow guiding element also serve to protect the device from contamination from the patient. That is, the protecting portion of the second flow guiding element prevents liquid, such as saliva or vomit, from the patient to reach into the device beyond the second flow guiding element. This is especially important for embodiments have a laminar flow section due to the narrow passageway(s).

The second flow guiding element is, correspondingly to the first flow guiding element, configured and arranged to prevent fluid flow into, or through, the second pressure connecting port by the shielding portion, while still providing a fluid passage, which is guided towards the flow constriction (typically towards the laminar flow section). Thus, the second pressure connecting port can be in fluid communication, without receiving any fluid flow, with fluid present between the second opening and the flow constriction via the at least one pressure conduit. Thus, the pressure of the fluid can be measured by a pressure sensor connected to the second pressure connecting port.

According to at least one example embodiment, the fluid passage is arranged between internal walls of the conduit and the protecting portion. Preferably, the fluid passage of the second flow guiding element is arranged in proximity to the internal walls of the conduit. Correspondingly, the protecting portion is preferably arranged closer to the center of the conduit compared to the fluid passage in order to efficiently hinder any liquid expectorated from the patient.

According to at least one example embodiment, the device further comprises a patient interface, such as e.g. a face mask, connected to the conduit at and end portion comprising the second opening.

That is, the conduit may comprise a first end portion arranged at the first opening, and a second end portion arranged at the second opening. Thus, the patient interface may be connected to, such as detachably connected to, or integrated with, the second end portion of the conduit such that the second opening lead into the void of the patient interface, such as e.g. the void of a face mask.

As already stated above, instead of a face mask, another patient interface such as e.g. an endotracheal tube, a laryngeal mask or nasal prongs may be chosen.

According to at least one example embodiment, the device is a single-use component, and is to be disposed after usage. Hereby, contamination between patients can be minimized.

According to at least one example embodiment, the device is injection molded. This provides for a suitable and cheap way of producing the device.

That is, the device is manufactured by an injection molding process. This is especially advantageous with regards to the specific geometry needed for the laminar flow section, such as the production of the plurality of channels. Specifically, the orientation of the pressure connecting ports, at least the respective portion arranged to face the first and second opening of the conduit, respectively, and the direction of the plurality of channels in the laminar flow section are aligned in the longitudinal direction of the conduit during the injection molding process.

According to at least one example embodiment, the device further comprises a pressure sensor unit detachably arranged to the conduit for measuring pressure upstream and/or downstream of the flow constriction.

Thus, the pressure sensor unit may measure the pressure difference over the flow constriction, i.e. at a location between the first opening and the flow constriction, and a location between the flow constriction and the second opening. Thus, the pressure sensor unit typically comprises channels enabling connections to the first and second pressure connecting ports, in order to transport the fluid pressure inside of the pressure sensor unit to a pressure sensor.

Advantageously, the pressure sensor unit is detachably arranged to the conduit via the pressure sensor connecting portion.

According to at least one example embodiment, the pressure sensor unit is not a part of the device, and is thus considered as a separate component to the device. For example, the device (without the pressure sensor unit) may be a single-use component (i.e. disposable) while the pressure sensor unit may be re-used.

According to at least one example embodiment, the pressure sensor unit may e.g. comprise a differential pressure sensor for measuring the differential pressure over the flow constriction by being in pressurized communication with the first and second pressure ports. The pressure sensor unit may alternatively or additionally comprise a gauge pressure sensor to assess the (positive) pressure used during ventilation. According to at least one example embodiment the gauge pressure sensor is realized using an absolute pressure sensor comparing the (ambient) pressure measured before ventilation, with the pressure during ventilation and then calculating the gauge pressure by subtracting these values. This allows for using only one (cheap yet accurate) barometric sensor to assess both ambient pressure and gauge pressure. According to at least one example embodiment, the pressure sensor unit comprises a pressure sensor preventing fluid flow through the pressure sensor by e.g. a membrane. Thus, the pressure sensor may be a membrane-based pressure sensor.

Moreover, the pressure sensor unit may comprise a battery, a CPU or processor, a memory, a wireless communication means, such as e.g. a Bluetooth module. The pressure sensor unit may furthermore comprise a housing holding all of the previously mentioned components of the pressure sensor unit.

As mentioned above, the device is configured and arranged so that there will be no fluid flow through the respective first and second pressure connecting ports. Thus, there will be no fluid flow in the pressure sensor unit when being attached to the conduit of the device. Typically, this would lead to poor zero level stability of pressure measurement. However, the laminar flow section mentioned above in accordance with an embodiment of the invention, counteracts this drawback, resulting in a satisfying accuracy of the flow measurement.

According to at least one example embodiment, the device comprises one or more filters arranged in the first and/or second pressure connecting ports. Hereby, contamination further into the pressure sensor unit is further prevented.

According to at least a third aspect of the present inventive concept, a respiration arrangement for breathing support to a patient, preferably an infant, is provided. The respiration arrangement comprises:
  a patient interface, such as a face mask adapted to fit over the mouth and nose of the patient,
  an air/gas source providing air or gas to the patient interface, and
  a device according to the first or second aspect of the inventive concept.

Effects and features related to the third aspect of the present inventive concept are largely analogous to those described above in connection with the first and second aspects of the inventive concept. For example, the air/gas source may e.g. be a resuscitation bag, and the patient interface may, instead of a face mask, be an endotracheal tube, a laryngeal mask or nasal prongs.

According to at least one example embodiment, the patient interface is a face mask which is connected to, such as detachably connected to, or integrated with, the second end portion of the conduit such that the second opening lead into the void of the face mask.

Further features of, and advantages with, the present inventive concept will become apparent when studying the appended claims and the following description. The skilled person realize that different features of the present inventive concept may be combined to create embodiments other than those described in the following, without departing from the scope of the present inventive concept.

BRIEF DESCRIPTION OF THE DRAWINGS

These and other aspects of the present inventive concept will now be described in more detail, with reference to the appended drawings showing an example embodiment of the inventive concept, wherein:

FIG. 4 illustrates in cross-section yet another device for a respiration arrangement according to at least one example embodiment of the inventive concept.

DETAILED DESCRIPTION OF EXAMPLE EMBODIMENTS

In the present detailed description, various embodiments of the inventive concept are mainly described with reference to a device for a respiration arrangement, and a respiration arrangement for breathing support to a patient, preferably an infant.

Figure 1:
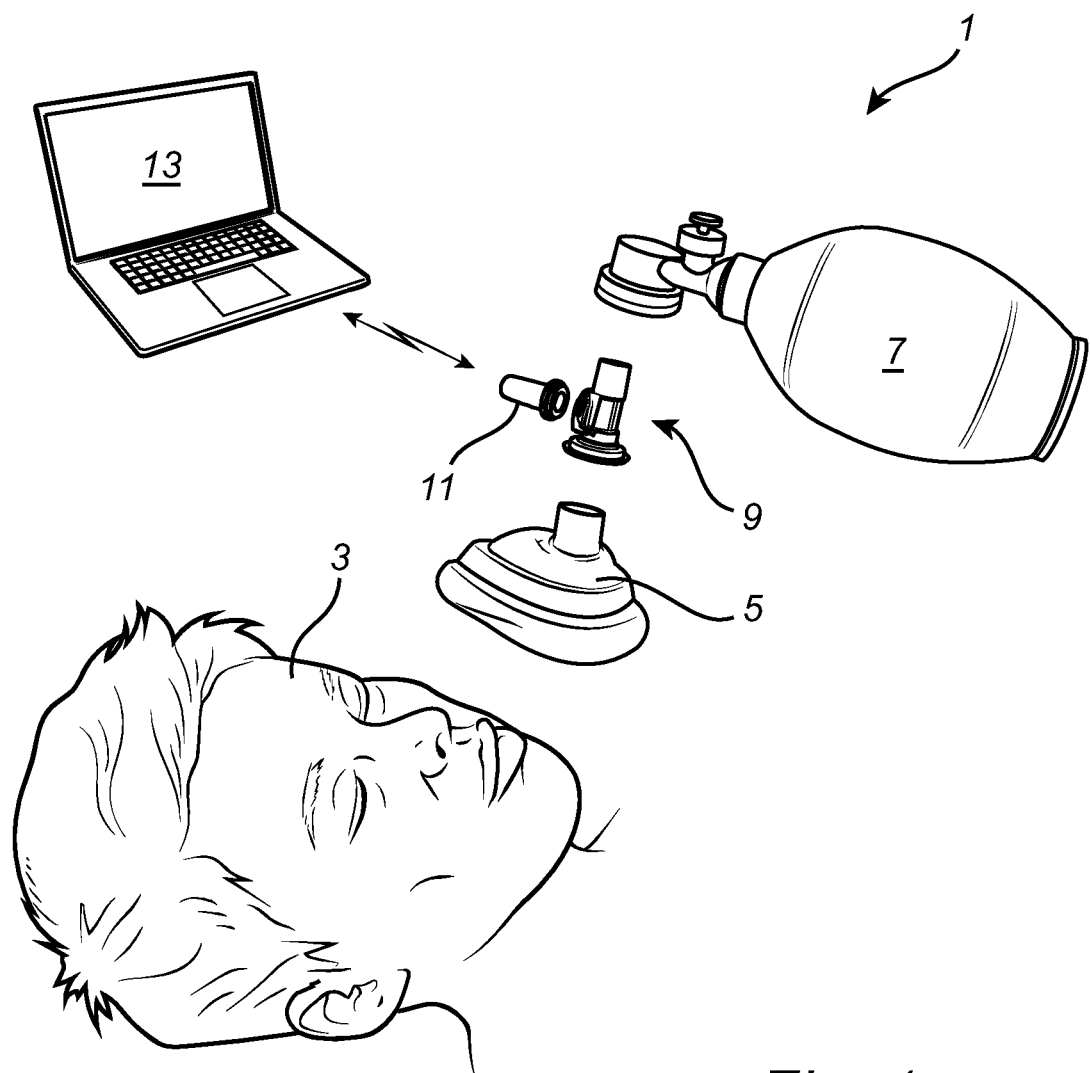
FIG. 1 schematically illustrates a respiration arrangement for breathing support to a patient, such as an infant, in accordance with at least one example embodiment of the inventive concept.

FIG. 1 is a schematic view illustrating a respiration arrangement 1 for breathing support to a patient 3, such as an infant 3. The respiration arrangement 1 comprises a face mask 5 adapted to fit over the mouth and nose of the patient 3, an air/gas source 7 providing air or gas to the face mask 5, and a device 9 providing an air/gas pathway from the air/gas source 7 to the face mask 5. Note that in FIG. 1, the device 9 is embodied as an airway adapter detachably connected to the face mask 5, but according to at least one example embodiment the face mask 5 is integrated with the airway adapter and thus forming a part of the device 9. The device 9 may e.g. be arranged with corresponding tubular portions in both ends of the device 9. That is, the end portion facing the face mask 5 may be tubular in a corresponding manner as the end portion facing the air/gas source, and thus not comprising the diverging portion presented in FIG. 1. The face mask 5 may be a separate/existing face mask or a soft mask, and/or the device 9 may form part of a hard mask connectable to a soft mask for forming an integrated device/face mask. The respiration arrangement 1 may further comprise a pressure sensor unit 11 detachably arranged to the device 9. According to at least one example embodiment of the inventive concept, the pressure sensor unit 11 is forming a part of the device 9. The pressure sensor unit 11 is typically used for measuring pressure generated by the fluid flowing through the device, which pressure can be used for calculating the fluid flow through the device, from the air/gas source 7 to the face mask 5, and thus the amount of air/gas fed to the patient 3 and/or calculating the fluid flow from the face mask 5 towards the air/gas source 7, i.e. the air/gas exhaled from the patient and transported in the other direction of the device 9. The pressure sensor unit 11 may for example comprise a differential pressure sensor, measuring the pressure drop over a flow constriction in the device (described in more detail with reference to FIG. 4). The respiration arrangement 1 may furthermore comprise a display 13, or another information presenting means, communicating with the pressure sensor unit 11. The display 13 is typically adapted to present the fluid flow through the device 9 and thus the amount of air/gas fed to the patient 3 and/or the amount of air/gas exhaled from the patient 3.

Figure 2:
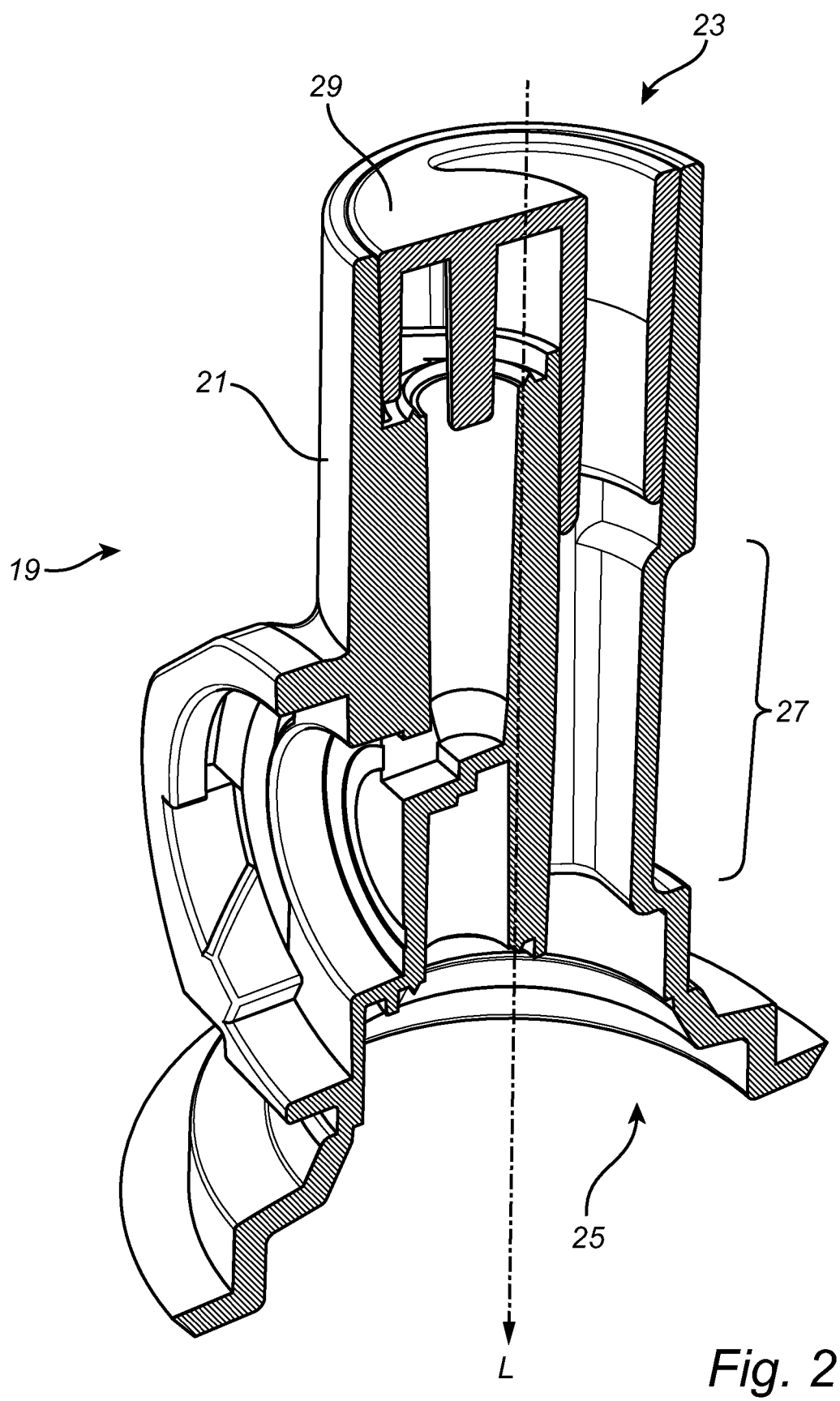
FIG. 2 illustrates in cross-section a device for a respiration arrangement according to at least one example embodiment of the inventive concept.
Figure 3:
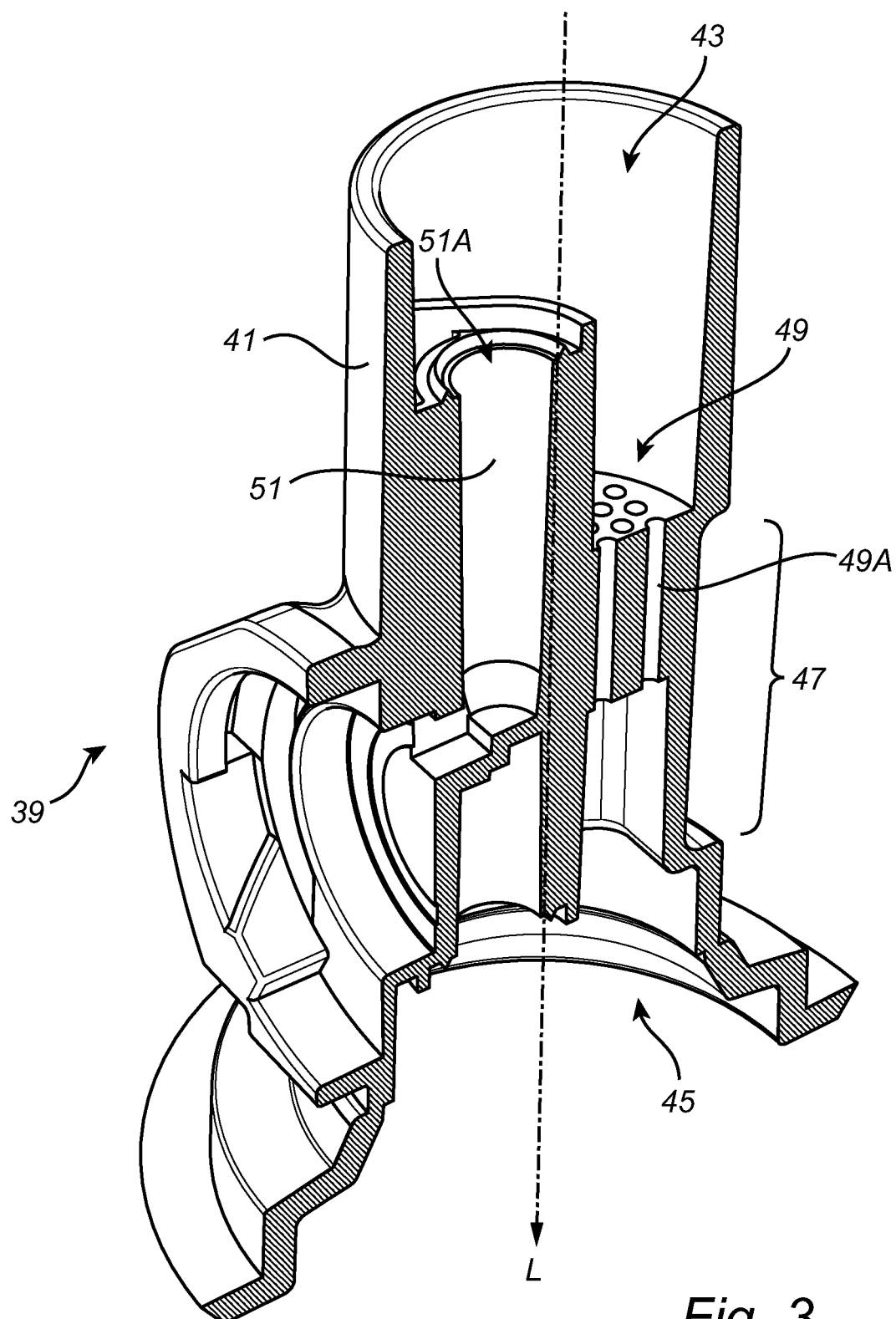
FIG. 3 illustrates in cross-section another device for a respiration arrangement according to at least one example embodiment of the inventive concept.

FIGS. 2-4 illustrates various embodiments of the device 9 of FIG. 1. In FIG. 2, the device 19 is illustrated in cross-section along the longitudinal direction L of the device 19. The device 19 comprises a conduit 21 having a first opening 23 connectable to a resuscitation bag or other gas source (shown in FIG. 1), and a second opening 25 connectable to a face mask (also shown in FIG. 1). Hereby, a fluid pathway is established along a longitudinal direction L of the conduit 21, from the first opening 23 to the second opening 25, and naturally, a fluid pathway from the second opening 25 to the first opening 23.

As seen in FIG. 2, the device 19 comprises a flow constriction 27, or flow restriction 27, in the conduit 21 which upon fluid flow through the conduit 21 results in a pressure difference over the flow constriction 27. The device 19 in FIG. 2 further comprises a flow guiding element 29 arranged in the conduit 21 between the flow constriction 27 and the first opening 23. The flow guiding element 29 is arranged to, upon fluid flow from the first opening 23 to the second opening 25, guide fluid flow to the flow constriction 27, which is described in more detail with reference to FIG. 5A. Hereby, any accuracy problem originating from the flow measurement with regards to asymmetrical geometry of the flow constriction 27, as e.g. flow constrictions not being centrally arranged in the conduit 21, or devices comprising other fluid ports (e.g. a pressure connecting port) risking by-pass of fluid or other disturbances (such as e.g. turbulent eddies), is mitigated. Thus, the flow guiding element 29 enables accurate measurement independently of the orientation of the incoming fluid flow to the device 19.

FIG. 3 illustrates a similar device 39 as the one shown in FIG. 2, but with the difference that there is no flow guiding element present in the device 39, and the flow constriction is designed differently. Thus, the device 39 comprises a conduit 41 having a first opening 43 connectable to a resuscitation bag or other gas source (shown in FIG. 1), and a second opening 45 connectable to a face mask (also shown in FIG. 1) whereby a fluid pathway is established along a longitudinal direction L of the conduit 41. In a similar manner as in FIG. 2, the flow constriction 47 in the conduit 41 of FIG. 3 is arranged to, upon fluid flow through the conduit, cause a pressure difference over the flow constriction 47. In FIG. 3, the flow constriction 47 comprises a laminar flow section 49, having a plurality of elongated channels 49A (only one of the channels is indicated in FIG. 3) arranged in the longitudinal direction L of the conduit 41.

The device 39 of FIG. 3 further comprises a pressure connecting port 51 arranged in pressurized communication with fluid between the flow constriction 47 and the first opening 43 (i.e. upstream of the flow constriction 47 when fluid flows from the first opening 43 to the second opening 45). The pressure connecting port 51 is arranged in the longitudinal direction L of the conduit 41. That is, the inlet 51A of the pressure connecting port 51 extends in a geometrical plane perpendicular to the longitudinal direction L of the conduit 41. Thus, the main direction of the pressure connecting port 51 is the same as the main direction of the plurality of elongated channels 49A. Hereby, manufacturing of the device 39 by e.g. injection molding is facilitated. Moreover, by having a pressure connecting port 51 with an inlet 51A facing the first opening 43 of the conduit, a filter, such as e.g. a bacteria filter, may easily be inserted into the device 39. However, it should be noted that according to at least one alternative embodiment of the inventive concept, the inlet 51A of the pressure connecting port 51 extends in a geometrical plane parallel to the longitudinal direction L of the conduit 41.

The pressure connecting port 51 is arranged and configured for being connected to a pressure sensor unit as shown in FIG. 4. Hereby, the pressure between the flow constriction 47 and the first opening 43 may be measured, which pressure can be used to determine the fluid flow through the conduit 41.

FIG. 4 illustrates a similar device 119 as those shown in FIGS. 2 and 3. Thus, the device 119 comprises a conduit 121 having a first opening 123 connectable to a resuscitation bag or other gas source (shown in FIG. 1), and a second opening 125 connectable to a face mask (also shown in FIG. 1) whereby a fluid pathway is established along a longitudinal direction L of the conduit 121. In a similar manner as in FIG. 2, the flow constriction 127 in the conduit 121 of FIG. 4 is arranged to, upon fluid flow through the conduit 121, cause a pressure difference over the flow constriction 127. In FIG. 4, the flow constriction 127 comprises a laminar flow section 128, having a plurality of elongated channels 128A (only one of the channels is indicated in FIG. 4) arranged in the longitudinal direction L of the conduit 121, in a similar manner as in FIG. 3.

As seen in FIG. 4, the device 119 comprises a first pressure connecting port 151 arranged in pressurized communication with fluid between the flow constriction 127 and the first opening 123, and a second pressure connecting port 153 arranged in pressurized communication with fluid between the flow constriction 127 and the second opening 125 (i.e. downstream of the flow constriction 127 when fluid flows from the first opening 123 to the second opening 127). The first pressure connecting port 151 is similar to the pressure connecting port 51 described with reference to FIG. 2. Thus, the first pressure connecting port 151 is arranged in the longitudinal direction L. That is, the inlet 151A of the first pressure connecting port 151 extends in a geometrical plane perpendicular to the longitudinal direction L of the conduit 121, and the main direction of the first pressure connecting port 151 is the same as the main direction of the plurality of elongated channels 128A. In a corresponding manner, the second pressure connecting port 153 is arranged in the longitudinal direction L, but with an inlet 153A facing in an opposite direction to the inlet 151A of the first pressure connecting port 151. Thus, the inlet 153A of the second pressure connecting port 153 is facing the second opening 125 of the conduit 121. Hence, also the inlet 153A of the second pressure connecting port 153 extends in a geometrical plane perpendicular to the longitudinal direction L of the conduit 121.

Thus, the first and the second pressure connecting ports 151, 153 are arranged in the device 119 to provide ports for upstream and downstream pressure, relative the flow constriction 127. As seen in FIG. 4, a pressure sensor unit 111 is illustrated as detachably arranged to the conduit 121. In more detail, the conduit 121 comprises a pressure sensor connecting portion 122 arranged and configured for connection to the pressure sensor unit 111. In FIG. 4, the pressure sensor connecting portion 122 is tube shaped and extends from the conduit 121 perpendicular to the longitudinal direction L. Moreover, the first and second pressure connecting ports 151, 153 are arranged in the device 119 to have their respective outlet 151B, 153B in the pressure sensor connecting portion 122, wherein the respective outlet 151B, 153B is facing in a direction perpendicular relative the respective inlet 151A, 153A of the first and second pressure connecting ports 151, 153. That is, the respective outlet 151B, 153B of first and second pressure connecting ports 151, 153 has a cross section parallel to the longitudinal direction L. However, it should be noted that the inlets 151A, 153A of the first and second pressure connecting ports are not arranged in the conduit to receive any fluid flow, but rather to act as a port for enabling fluid communication enabling measurement of the pressure of the fluid upstream and downstream of the flow constriction. Correspondingly, the outlets 151B, 153B of the first and second pressure connecting ports 151, 153 are not arranged in the conduit 121 to discharge any fluid flow, but rather to act as a port for enabling fluid communication to the pressure sensor in the pressure sensor unit 111.

By providing the first and second pressure connecting ports 151, 153 arranged in the device 119 to provide ports for upstream and downstream pressure, relative the flow constriction 127, as shown in FIG. 4, the differential pressure over the flow constriction 127 can be measured by a differential pressure sensor comprised in the pressure sensor unit 111. The pressure sensor unit may e.g. comprise a battery, a CPU or processor, a memory, a wireless communication means, such as e.g. a Bluetooth module, and a battery. The pressure sensor unit 111 and flow constriction 127 may be referred to as a monitoring arrangement, which together with an information presenting means (as shown in FIG. 1 as a display 13), are arranged to calculate and present the amount of air/gas flowing to/from the patient.

The device 119 in FIG. 4 comprises a first flow guiding element 129 arranged in the conduit 121 between the flow constriction 127 and the first opening 123 and configured to guide fluid flow from the first opening 123 towards the flow constriction 127 when fluid flows from the first opening 123 towards the second opening 125, and comprises a second flow guiding element 131 arranged in the conduit 121 between the flow constriction 127 and the second opening 125 and configured to guide fluid flow from the second opening 125 towards the flow constriction 127 when fluid flows from the second opening 125 towards the first opening 123. The first flow guiding element 129 corresponds in large to the flow guiding element 29 of the device 19 of FIG. 2. Thus, the first flow guiding element 129 is arranged and configured to guide fluid flow to the flow constriction 127 to mitigate any accuracy problem originating from the flow measurement with regards to asymmetrical geometry of the flow constriction 127, or as here, with regards to undesirable fluid flow into the first pressure connecting port 151. Thus, the first flow guiding element 129 enables accurate measurement independently of the orientation of the incoming fluid flow, via the first opening 123, to the device 119.

The second flow guiding element 131, is configured to guide fluid flow to the flow constriction 127 to mitigate any accuracy problem originating from the flow measurement with regards to asymmetrical geometry of the flow constriction 127, or as here, with regards to undesirable fluid flow into the second pressure connecting port 153. Thus, the second flow guiding element 131 enables accurate measurement independently of the orientation of the incoming fluid flow, via the second opening 125, to the device 119.

Figure 5A:
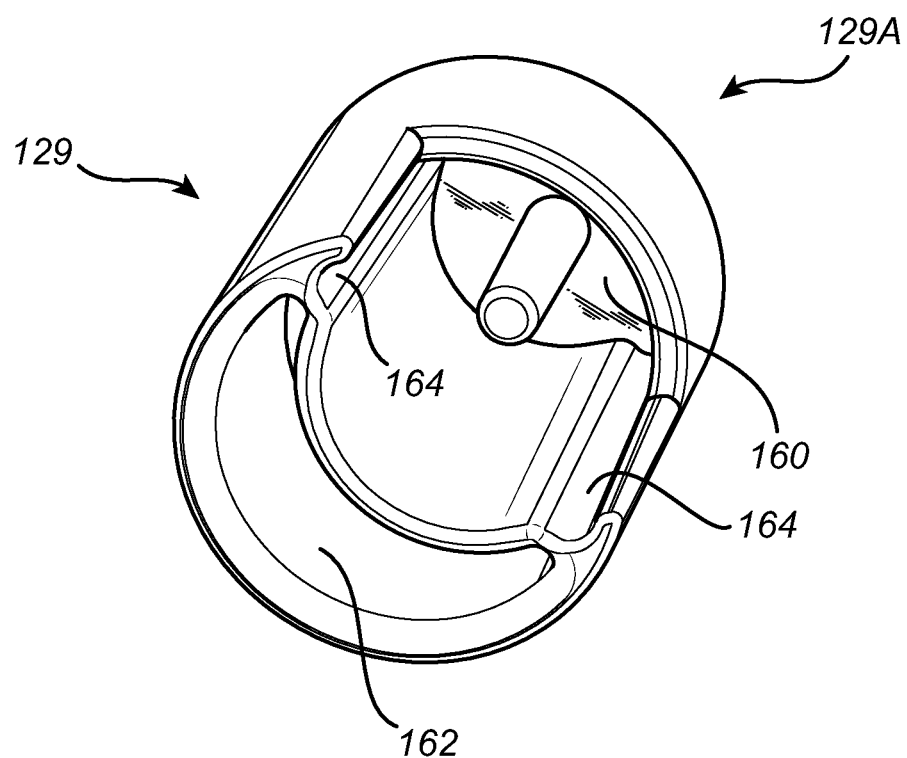
FIGS. 5A and 5B illustrate perspective views of the first and second flow guiding elements.
Figure 5B:
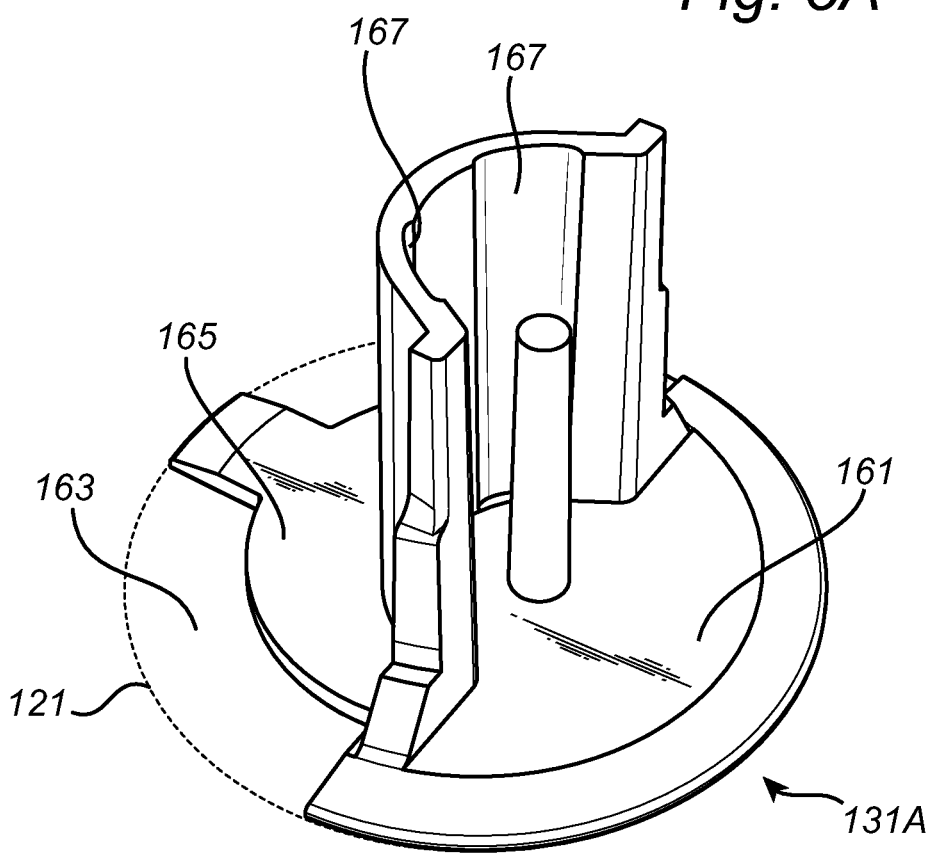

FIG. 5A and FIG. 5B illustrates detailed views of the first flow guiding element 129 and the second flow guiding element 131, respectively.

The first flow guiding element 129 comprises a first surface 129A facing the first opening 123 when being arranged in the conduit 121 of the device 119, wherein the first surface 129A comprising a shielding portion 160. The first flow guiding element 129 is arranged and configured in the conduit 121 such that the shielding portion 160 covers the first pressure connecting port 151, or at least the inlet 151A of the first pressure connecting port 151. Hereby, fluid flow into the first pressure connecting port 151 can be avoided by the shielding portion 160.

The first flow guiding element 129 further comprises a fluid passage 162 enabling fluid flow between the first opening 123 and the flow constriction 127 when being arranged in the conduit 121 of the device 119. The first flow guiding element 129 is arranged and configured in the conduit 121 such that the fluid passage 162 covers the flow constriction 127, or at least guides the fluid flow towards the flow constriction 127 when fluid flows through the device 119 from the first opening 123 to the second opening 125. In FIG. 5A, the fluid passage 162 is shaped to enable a minimum flow resistance by having a crescent shaped cross section (cross section being perpendicular to the longitudinal direction L of the conduit 121).

Moreover, in the embodiment of FIG. 5A, the first flow guiding element 129 comprises two pressure conduits 164 arranged in proximity to an end portion of the fluid passage 162 to provide fluid channels between the fluid passage 162 and the first pressure connecting port 151. The pressure conduits 164 enables the first pressure connecting port 151 to be in fluid communication, without receiving any fluid flow, with fluid present between the first opening 123 and the flow constriction 127. Thus, the pressure of the fluid can be measured by a pressure sensor connected to the first pressure connecting port 151.

As can be seen in FIG. 5B, the second flow guiding element 131 comprises a first surface 131A facing the second opening 125 when being arranged in the conduit 121 of the device 119, wherein the first surface 131A comprising a shielding portion 161. The second flow guiding element 131 is arranged and configured in the conduit 121 such that the shielding portion 161 covers the second pressure connecting port 153, or at least the inlet 153A of the second pressure connecting port 153. Hereby, fluid flow into the second pressure connecting port 153 can be avoided by the shielding portion 161.

The second flow guiding element 131 further comprises a fluid passage 163 enabling fluid flow between the second opening 125 and the flow constriction 127 when being arranged in the conduit 121 of the device 119. The second flow guiding element 131 is arranged and configured in the conduit 121 such that the fluid passage 163 covers at least a part of the flow constriction 127, or at least guides the fluid flow towards the flow constriction 127 when fluid flows through the device 119 from the second opening 125 to the first opening 123.

The second flow guiding element 131 further comprises a protecting portion 165 arranged and configured in the conduit 121 to cover at least a part of the flow constriction 127, and thereby preventing liquid, such as saliva or vomit, from the patient to reach into the device 119 beyond the second flow guiding element 131.

In FIG. 5B, the fluid passage 163 is arranged between internal walls of the conduit 121 and the protecting portion 165. In the embodiment in FIG. 5B, the fluid passage 163 of the second flow guiding element 131 is arranged in proximity to the internal walls of the conduit 121, and the protecting portion 165 is arranged closer to the center of the conduit 121. Herby, the protecting portion 165 can efficiently hinder any liquid expectorated from the patient.

Moreover, in the embodiment of FIG. 5B, the second flow guiding element 131 comprises two pressure conduits 167 arranged to provide fluid channels between fluid present between the second opening 125 and the flow constriction 127, and the second pressure connecting port 153. The pressure conduits 167 enables the second pressure connecting port 153 to be in fluid communication, without receiving any fluid flow, with fluid present between the second opening 125 and the flow constriction 127. Thus, the pressure of the fluid can be measured by a pressure sensor connected to the second pressure connecting port 153.

It should be noted that the air/gas source 7 may e.g. be an air source 7, or another type of gas source providing e.g. oxygen. In one example embodiment, the air/gas source 7 is a resuscitation bag/bellow 7 or a T-piece resuscitator.

Even though the inventive concept has been described with reference to specific exemplifying embodiments thereof, many different alterations, modifications and the like will become apparent for those skilled in the art. Also, it should be noted that parts of the pressure sensor unit 11, 111 may be omitted, interchanged or arranged in various ways, the device 9, 119 yet being able to perform the functionality of the present inventive concept. Moreover, the patient interface may instead of a face mask be an endotracheal tube, a laryngeal mask or nasal prongs.

Additionally, variations to the disclosed embodiments can be understood and effected by the skilled person in practicing the claimed inventive concept, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage.

The invention claimed is:

1. A device for a respiration arrangement comprising:
   a conduit having a first opening connectable to an air/gas source, and a second opening connectable to a patient interface, such that a fluid pathway along a longitudinal direction of the conduit is established from the first opening to the second opening;
   a flow constriction arranged in the conduit which upon fluid flow through the conduit results in a pressure difference over the flow constriction; and
   a first flow guiding element arranged in the conduit between the first opening and the flow constriction, and configured to guide fluid flow to the flow constriction,
   wherein the flow constriction at least partly comprises a laminar flow section,
   wherein the device further comprises at least one pressure connecting port arranged in pressurized communication with fluid between the flow constriction and the first opening, the at least one pressure connecting port configured to connect to a pressure sensor for measuring fluid pressure, and wherein the at least one pressure connecting port is arranged in the longitudinal direction of the conduit, and
   wherein the first flow guiding element comprises:
      a shielding portion arranged in the conduit to cover an inlet of the at least one pressure connecting port,
      a fluid passage enabling fluid flow between the first opening and the flow constriction, and
      at least one pressure conduit arranged to provide a fluid channel between the fluid passage and the at least one pressure connecting port.

2. The device according to claim 1, wherein the at least one pressure connecting port is a first pressure connecting port, and the device further comprises a second pressure connecting port arranged in pressurized communication with fluid between the flow constriction and the second opening, such that the pressure sensor is configured to connect to the first and second pressure connecting ports for measuring the differential pressure over the flow constriction.

3. The device according to claim 1, wherein the laminar flow section comprises a plurality of elongated channels arranged in the longitudinal direction of the conduit such that the at least one pressure connecting port and the plurality of elongated channels are arranged at least partly in parallel.

4. The device according to claim 1, further comprising a patient interface in the form of a face mask connected to the conduit at an end portion comprising the second opening.

5. The device according to claim 1, wherein the device is injected molded.

6. The device according to claim 1, further comprising the pressure sensor, the pressure sensor being detachably arranged to the conduit for measuring pressure upstream and/or downstream of the flow constriction.

7. A respiration arrangement for breathing support to a patient, comprising:
a patient interface adapted to fit over the mouth and nose of the patient,
an air/gas source providing air or gas to the patient interface, and
a device according to claim 1.

8. A device for a respiration arrangement, comprising:
a conduit having a first opening connectable to an air/gas source, and a second opening connectable to a patient interface, such that a fluid pathway along a longitudinal direction of the conduit is established from the first opening to the second opening;
a flow constriction arranged in the conduit which upon fluid flow through the conduit results in a pressure difference over the flow constriction;
a first flow guiding element arranged in the conduit between the first opening and the flow constriction, and configured to guide fluid flow to the flow constriction; and
a second flow guiding element arranged in the conduit between the flow constriction and the second opening, and configured to guide fluid flow away from the second pressure connecting port,
wherein the flow constriction at least partly comprises a laminar flow section,
wherein the device further comprises at least one pressure connecting port arranged in pressurized communication with fluid between the flow constriction and the first opening, the at least one pressure connecting port configured to connect to a pressure sensor for measuring fluid pressure, and wherein the at least one pressure connecting port is arranged in the longitudinal direction of the conduit, and
wherein the at least one pressure connecting port is a first pressure connecting port, and the device further comprises a second pressure connecting port arranged in pressurized communication with fluid between the flow constriction and the second opening, such that the pressure sensor is configured to connect to the first and second pressure connecting ports for measuring the differential pressure over the flow constriction.

9. The device according claim 8, wherein the second flow guiding element comprises:
a shielding portion arranged in the conduit to cover an inlet of the second pressure connecting port,
a fluid passage enabling fluid flow between the second opening and the flow constriction,
at least one pressure conduit arranged to provide a fluid channel between the fluid passage and the second pressure connecting port, and
a protecting portion arranged in the conduit to prevent any liquid expectorated from the patient to reach further into the conduit.

10. A device for a respiration arrangement comprising:
a conduit having a first opening connectable to an air/gas source, and a second opening connectable to a patient interface, such that a fluid pathway along a longitudinal direction of the conduit is established from the first opening to the second opening;
a flow constriction, arranged in the conduit which upon fluid flow through the conduit results in a pressure difference over the flow constriction; and
at least one pressure connecting port arranged in pressurized communication with fluid between the flow constriction and the first opening, the at least one pressure connecting port configured to connect to a pressure sensor for measuring fluid pressure, and wherein the at least one pressure connecting port is arranged in the longitudinal direction of the conduit,
wherein the device further comprises a first flow guiding element arranged in the conduit between the first opening and the flow constriction, and configured to guide fluid flow to the flow constriction, and
wherein the first flow guiding element comprises:
a shielding portion arranged in the conduit to cover an inlet of the at least one pressure connecting port,
a fluid passage enabling fluid flow between the first opening and the flow constriction, and
at least one pressure conduit arranged to provide a fluid channel between the fluid passage and the at least one pressure connecting port.

11. The device according to claim 10, wherein the at least one pressure connecting port is a first pressure connecting port, and the device further comprises a second pressure connecting port arranged in pressurized communication with fluid between the flow constriction and the second opening, such that the pressure sensor is configured to connect to the first and second pressure connecting ports for measuring the differential pressure over the flow constriction.

12. The device according to claim 10, further comprising a patient interface in the form of a face mask connected to the conduit at and end portion comprising the second opening.

13. The device according to claim 10, wherein the device is injected molded.

14. The device according to claim 10, further comprising a pressure sensor detachably arranged to the conduit for measuring pressure upstream and/or downstream of the flow constriction.

15. A device for a respiration arrangement, comprising:
a conduit having a first opening connectable to an air/gas source, and a second opening connectable to a patient interface, such that a fluid pathway along a longitudinal direction of the conduit is established from the first opening to the second opening;
a flow constriction, arranged in the conduit which upon fluid flow through the conduit results in a pressure difference over the flow constriction;
a first pressure connecting port arranged in pressurized communication with fluid between the flow constriction and the first opening, the first pressure connecting port configured to connect to a pressure sensor for measuring fluid pressure, and wherein the first pressure connecting port is arranged in the longitudinal direction of the conduit;

a second pressure connecting port arranged in pressurized communication with fluid between the flow constriction and the second opening, such that the pressure sensor is configured to connect to the first and second pressure connecting ports for measuring the differential pressure over the flow constriction;

a first flow guiding element arranged in the conduit between the first opening and the flow constriction, and configured to guide fluid flow to the flow constriction; and a second flow guiding element arranged in the conduit between the flow constriction and the second opening, and configured to guide fluid flow away from the second pressure connecting port.

16. The device according claim 15, wherein the second flow guiding element comprises:

a shielding portion arranged in the conduit to cover an inlet of the second pressure connecting port, a fluid passage enabling fluid flow between the second opening and the flow constriction, at least one pressure conduit arranged to provide a fluid channel between the fluid passage and the second pressure connecting port, and a protecting portion arranged in the conduit to prevent any liquid expectorated from the patient to reach further into the conduit.

* * * * *